(12) United States Patent
Heaton et al.

(10) Patent No.: US 7,461,032 B2
(45) Date of Patent: Dec. 2, 2008

(54) DETECTION METHODS AND SYSTEMS USING SEQUENCED TECHNOLOGIES

(75) Inventors: Michael A. Heaton, Owego, NY (US); David Most, Endicott, NY (US); Shawn Younkin, Owego, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 299 days.

(21) Appl. No.: 11/343,492

(22) Filed: Jan. 31, 2006

(65) Prior Publication Data

US 2006/0262901 A1    Nov. 23, 2006

Related U.S. Application Data

(63) Continuation-in-part of application No. 10/705,445, filed on Nov. 11, 2003, now Pat. No. 7,023,956.

(60) Provisional application No. 60/425,615, filed on Nov. 11, 2002.

(51) Int. Cl.
*G06N 5/00* (2006.01)
(52) U.S. Cl. .......................................... 706/10; 706/45
(58) Field of Classification Search .................. 706/10; 382/156; 367/131; 342/64
See application file for complete search history.

(56) References Cited

U.S. PATENT DOCUMENTS

| | | | |
|---|---|---|---|
| 4,756,866 A | 7/1988 | Alvarez | 376/157 |
| 4,864,142 A | 9/1989 | Gomberg | 250/390.04 |
| 5,319,547 A | 6/1994 | Krug et al. | 364/409 |
| 5,341,142 A * | 8/1994 | Reis et al. | 342/64 |
| 5,367,552 A | 11/1994 | Peschmann | 378/57 |
| 5,479,023 A | 12/1995 | Bartle | 250/390.04 |
| 5,488,589 A * | 1/1996 | DeAngelis | 367/131 |
| 5,497,430 A * | 3/1996 | Sadovnik et al. | 382/156 |
| 5,600,303 A | 2/1997 | Husseiny et al. | 340/568 |
| 5,600,700 A | 2/1997 | Krug et al. | 378/57 |
| 5,642,393 A | 6/1997 | Krug et al. | 378/57 |
| 5,692,029 A | 11/1997 | Husseiny et al. | 378/88 |
| 5,838,759 A | 11/1998 | Armistead | 378/57 |
| 5,974,111 A | 10/1999 | Krug et al. | 378/57 |
| 6,026,340 A | 2/2000 | Corrado et al. | 701/47 |
| 6,035,014 A | 3/2000 | Hiraoglu et al. | 378/57 |
| 6,088,423 A | 7/2000 | Krug et al. | 378/57 |
| 6,334,095 B1 | 12/2001 | Smith | 702/181 |
| 6,370,222 B1 | 4/2002 | Cornick, Jr. | 378/57 |
| 6,430,255 B2 | 8/2002 | Fenkart et al. | 378/57 |
| RE37,899 E | 11/2002 | Grodzins et al. | 378/86 |
| 6,515,582 B1 | 2/2003 | Teowee et al. | 340/426.1 |
| 7,170,418 B2 * | 1/2007 | Rose-Pehrsson et al. | 340/628 |
| 2002/0018542 A1 | 2/2002 | Fenkart et al. | 378/57 |
| 2002/0071524 A1 | 6/2002 | Renkart et al. | 378/199 |
| 2002/0097835 A1 | 7/2002 | Fenkart et al. | 378/57 |
| 2002/0172324 A1 | 11/2002 | Ellengogen | 378/57 |
| 2004/0078101 A1 | 4/2004 | Kondoh et al. | 702/40 |

FOREIGN PATENT DOCUMENTS

JP        09304543        11/1997

* cited by examiner

*Primary Examiner*—Wilbert L Starks, Jr.
(74) *Attorney, Agent, or Firm*—Burns & Levinson LLP; Jacob N. Erlich; Orlando Lopez

(57) ABSTRACT

Methods and systems for interconnecting sub-systems and for identifying combinations of multiple technologies.

14 Claims, 9 Drawing Sheets

Figure 3

|  | Explosive Detector Output | |
| --- | --- | --- |
|  | OK | Alarm |
| Object Input — No Explosive | 1-PFA | PFA |
| Object Input — With Explosive | 1-PD | PD |

| Input | Type | Output OK | Output Alarms |
|-------|------|-----------|---------------|
| 100 | Explosive | 10 | 90 |
| 100 | Non-Explosive | 90 | 10 |

(Assuming system has PD= 90% and PFA = 10%)

Level 2 Alarm Mitigation System. (Assuming all sub-systems have PD= 90% and PFA = 10%)

Majority System strategy. (Assuming all sub-systems have PD= 90% and PFA = 10%)

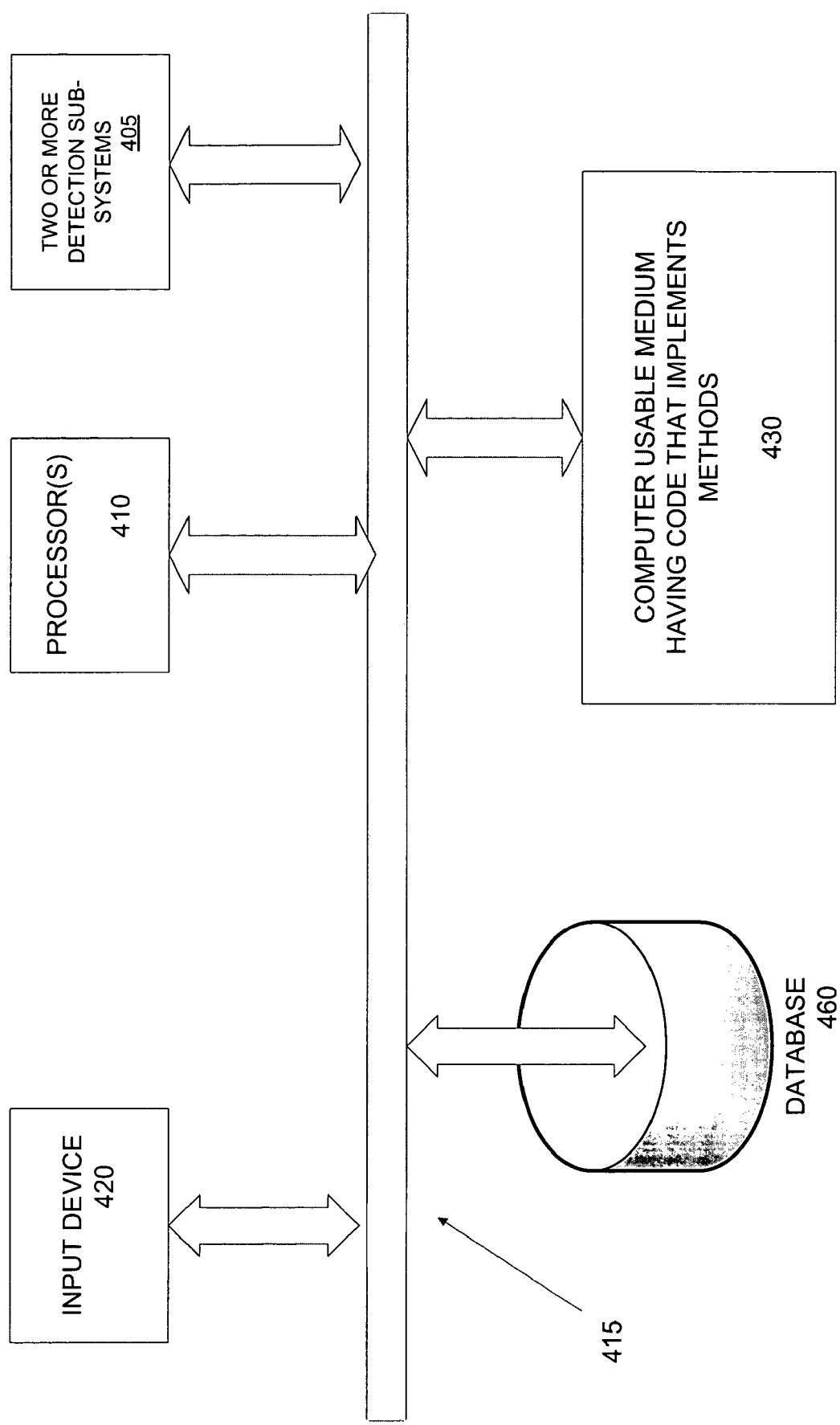

DETECTION METHODS AND SYSTEMS USING SEQUENCED TECHNOLOGIES

CROSS REFERENCE TO RELATED APPLICATIONS

This application is a continuation in part of U.S. patent application Ser. No. 10/705,445 filed on Nov. 11, 2003, which is herein incorporated by reference.

BACKGROUND OF THE INVENTION

This invention relates generally to the detection of a presence of a characteristic in an object, and, more particularly to the application of sequenced technologies to detection of a presence of a characteristic in an object.

Detection of the presence of a characteristic in an object is a common function in a variety of applications. Exemplary applications, while not being an exhaustive listing, include detection of a particular disease at a location in a patient, detection and tracking of targets in military applications, detection of obstacles and objects in robotics and in automotive applications such as self closing sunroofs or doors.

An example of detection of the presence of a characteristic in an object is the detection of an undesired substance within an object, such as detection of explosives inside objects. Recently there has been increased awareness of the potential for large-scale introduction of explosives to create chaos or to harm an intended set of victims. There are currently a variety of technologies available to detect the presence of explosives. However, systems utilizing a single technology do not effectively measure all explosive types or meet the desired accuracy. In general, systems utilizing a single technology do not usually meet the desired conditions for the detection of a presence of a characteristic in an object. Combining technologies will not always result in improved performance. Data Fusion techniques can be used to provide guidance in the combination but such techniques require large computational resources and/or learning strategies.

There is a need for simpler strategies for interconnecting detection systems, where each system utilizes a single technology, hereinafter referred to as sub-systems, and for combination systems designed according to that simpler strategy.

Background on Explosive Detection Technologies

Since an important example of detection of the presence of a characteristic in an object is the detection of explosives inside objects, in order to better understand the descriptions of systems and methods for the detection of explosives inside objects, a background discussion of explosive detection technologies is provided herein below.

Explosive Detection Technologies

The Explosive Detection Systems (EDS) considered are based on X-ray technologies, Neutron-Based Bulk Explosives Detection technologies, Other Nuclear (non-neutron) Bulk Explosive technologies, Nuclear Quadrupole Resonance technologies, and Trace Detection technologies.

X-Ray Technologies

X-ray Imaging, Dual Energy X-ray Imaging, Computed Tomography (CT), Dual Energy CT, backscatter radiography, and diffraction radiography all rely on x-rays penetrating into objects being transmitted, absorbed, scattered, or diffracted. Each of these processes has been exploited as an explosive detection system (EDS) technology.

X-ray Imaging

Projection x-ray imaging uses a conventional x-ray source exposing objects in tubs or sacks. The portion of the x-rays that pass through the objects are detected and converted to digital data and a visible image. The attenuation of x-rays is described by $$(1 - Io/Ii = e^{(-\mu x)})$$

where Io is the output x-ray intensity, Ii is the input x-ray intensity, e is the natural log base, $\mu$ is the linear x-ray attenuation coefficient (1/cm), and x is the x-ray path length (cm). The $\mu x$ is actually the sum of the linear x-ray attenuation coefficients of each material in the x-ray path multiplied by the path length of each material. Each linear x-ray attenuation coefficient is a function of the material density and effective atomic number (Z). Many explosives have a density about 1.6 g/cm$^3$ and similar materials (N, O, C, and H) so explosives tend to look similar in x-ray images. Unfortunately, many other materials have linear x-ray attenuation coefficients similar to explosives, including organics and plastics. A thin high density material can look the same as a thick low density material. Although projection x-ray imaging is not used for explosive detection, x-ray imaging can be used for identifying shapes and objects related to bombs such as detonators, timers, batteries, and wires. Although such objects can be hidden using an x-ray absorbing material, such as lead, to block the x-rays, the lead shield would be visible in x-ray images and would cause a lack of penetration alarm.

Dual Energy X-rays Imaging

The linear x-ray attenuation coefficient of each material is a function of the x-ray energy, density, and effective atomic number. If x-ray image data is acquired with two or more x-ray energies (KV's) then for each picture element (pixel) the density and effective atomic number can be calculated. Using the density and effective Z gives improved ability to discern explosives from similar materials. The density and effective Z are still averaged over the entire path of the x-rays, so a thin high density material can look the same as a thick low density material.

Computed Tomography (CT)

CT data is acquired by measuring the x-ray attenuation thru the object being examined from many different positions and angles. The x-rays can form a cone beam, fan beam, or pencil beam. The x-rays can be detected as an area, a strip, a line, or a single point. An x-ray source emits x-rays that are attenuated as they pass through the object being examined. The intensity of the x-rays exiting the object are measured by the detectors, digitized, and fed to a computer along with position information. The computer uses the x-ray three dimensional vector information to determine the location of each voxel (volume element) that each x-ray passed through. The process called back projection adds part of each x-ray measurement to each of the voxels (volume elements) that the x-rays passed through. The result is a 3 dimensional (3D) reconstruction of the object being examined. The linear x-ray attenuation coefficient, $\mu$, is estimated for every voxel. More x-rays and more angles passing thru a voxel give better estimates of u. CT provides a 3D array of measured x-ray attenuation coefficients as a function of position. As with projection x-ray, the x-ray attenuation coefficient is directly related to the material in the voxels. CT has an advantage over projection x-ray in that instead of averaging over the entire x-ray path, there is an x-ray attenuation coefficient for each voxel. Smaller voxels make it less likely that more than one material is in the voxel and likelihood of correctly interpreting the material is improved. The CT x-ray source and detector can be mounted on a gantry, which rotates around the object being examined. Similarly, the CT x-ray source and detector can be fixed where the object being examined is rotated. Typically, a fan beam is used with a line detector on a gantry to gather slice data and the object is translated on a conveyor to acquire multiple slices. It should be noted that the CT X-ray source could also be a cone beam source. Furthermore, it should be realized that the above embodiments are sample embodiments and that other embodiments are possible. If the conveyor is fixed during acquisition the result is a slice and if the conveyor is moving the result is a helical scan.

Alternatively, the CT can use multiple x-ray sources and multiple detector arrays to eliminate the need for a rotation. Fix source CT has advantages of less moving parts, higher speed, higher mechanical reliability and disadvantages of lower electrical reliability, more electrical parts, less accurate reconstructions due to fewer measurements. Each configuration requires specialized algorithms for back projection and reconstruction. All CT configurations measure the x-ray attenuation coefficient for each voxel, however some systems produce small voxels covering the entire volume while some have space in between the voxels and some systems only look at the parts of the volumes that were found to be suspect by other technologies. All are types of CT, but their capabilities vary widely.

Dual Energy CT

Two sets of CT data acquired using two different x-ray energies can be used to generate reconstructions for the two energy levels. The linear x-ray attenuation coefficients for the two energies for each voxel can be used to solve for the density and effective atomic number of each voxel. The density and effective atomic number can give a more accurate indication of the material in the voxel than just x-ray attenuation coefficients of single energy CT. Dual Energy CT (DECT) is more effective than dual energy projection x-ray because multiple materials are less likely to be found in a voxel than in an entire x-ray path of projection x-ray images. Multiple energies can be used to further enhance the data quality, but not by much. X-ray sources generally emit wide spectrums of x-ray energy that tend to overlap and blur the value of more than two energies. The compromise with DECT is that widely separated energies work better, but widely separated means that one energy must be lower energy and the lower energy may not penetrate the object being examined as well. The number of x-ray photons may be too low to give a useful improvement in the probability of detection and probability of false alarm for explosive detection in some objects.

Backscatter Radiography

When x-rays enter a material some of the x-rays are absorbed by materials and reemitted (scattered) at lower energy in all directions. Those x-rays returning to near the x-ray source are called backscatter. A collimated pencil beam x-ray source is used to determine the location doing the backscattering. Scanning the x-ray pencil beam can produce an image of the backscattered x-rays. Backscatter images are particularly good at imaging lower density materials such as organics, plastics, and explosives. Backscatter imaging can not distinguish between the material types. Scanning pencil beam imaging systems, such as those used in backscattering imaging systems, may simultaneously produce a transmission or projection x-ray image which is useful in for identifying shapes and objects related to bombs such as detonators, timers, batteries, and wires. Backscattering is a self-filtering process so the farther into the object being examined the x-rays travel, the less sensitive backscatter image is.

Diffraction Radiography

When x-rays entering a material encounter crystalline materials, the x-rays are bent or diffracted in a direction dependent on the material. Some explosives components are crystals and can be detected by the diffraction angle of the x-rays. X-rays are diffracted by many other common materials including metals, sand, gems, medicine, some papers, and photos. Thick materials give wide diffuse diffraction angles making it hard to distinguish one material from another. Simply detecting crystalline materials gives insufficient explosive detection specificity. This is another technology that is useful in the lab and with special test objects, but may be difficult to use in a real application.

Neutron-Based Bulk Explosives Detection Technologies

The basic principles behind the neutron-based Explosives Detection Systems (EDS) are the following: (1) a beam of neutrons enters the package to be inspected, (2) the neutrons interact with nuclei present in the explosives, (3) as a result of the interaction, either (a) new radiation, characteristic of the target nucleus, is produced, and/or (b) a deflection or absorption of the neutron beam occurs, (4) the new radiation and/or the neutron beam exiting the target is detected, and (5) computer analysis of the outgoing particles is used to deduce the presence of the explosive. All of the neutron-based techniques try to detect explosives by detecting and quantifying the atomic components of explosives, nitrogen (N), oxygen (O), carbon (C) and hydrogen (H). The main signature for explosives is the relatively high concentration of nitrogen and secondarily oxygen, and the relatively low concentration of carbon and hydrogen, as compared to common materials. The various neutron-based technologies differ in the radiation (referred to in step 3, above) they use to deduce the presence of one or more of N, O, C and H, the properties of the neutron beam whose interaction produces the radiation, and the method, if any, used to localize (i.e., image) those materials within the package being inspected. In the following, a brief description of the theoretical basis of each of the neutron-based technologies is provided, starting with the most mature technology and ending with the least.

Thermal Neutron Analysis (TNA)

In TNA the detected radiation is a gamma ray. The neutron interaction producing that gamma ray is the capture of the neutron by the nucleus; for example, the isotope $^{14}N$ captures a neutron to become $^{15}N$. Although $^{15}N$ is a stable isotope, it is initially produced in a very highly excited state, which subsequently (within $10^{-17}$ S of the capture) decays to its stable state, producing a number of gamma rays, the most energetic of which has energy of 10.8 MeV. The probability of neutron capture is (usually) highest for the slowest neutrons; the slowest that a neutron inside a target can be is when its energy is the same as the average thermal energy of the target, hence the name TNA. The cross section for thermal capture on $^{14}N$ is 75 mb[1], on $^{16}O$ 0.19 mb, on $^{12}C$ 3.53 mb, and on $^{1}H$ 333 mb. (The cross section is a measure of the likelihood that a process take place; the above numbers indicate that for an equal number of atoms, a thermal neutron is 75 mb/0.19 mb=394 times more likely to be captured by a $^{14}N$ nucleus than by an $^{16}O$ nucleus, and 333 mb/75 mb=4.4 times as likely to be captured by a $^{1}H$ nucleus than by a $^{14}N$ nucleus.) These cross sections indicate that TNA is primarily sensitive to the N component of explosives and not to the O content. Thus the presence of relatively small quantities of N-rich substances such as Polyurethane or Melamine, or large quantities of substances containing small-to-moderate concentrations of N, such as Orlon, silk and wool, can trigger a false alarm in a TNA system.

[1] For N, thermal capture produces a 10.8 MeV gamma ray only 14% of the time, so the effective cross section for that signature is 0.14*75=11 mb.

The neutron source for TNA could be a radioactive source or an accelerator based source (the term Electronic Neutron Generator, or ENG, is sometimes used in the industry to refer to accelerator-based neutron sources). The most suitable radioactive source for TNA is the fission source *Californium* 252, $^{252}Cf$, which produces $2.30\times10^6$ n/s per microgram. The energy distribution of the emitted neutrons peaks between 0.5 and 1.0 MeV and extends to as high as 10 MeV, with the intensity dropping almost exponentially with increasing neutron energy. Thus the size of the source is determined by the encapsulation requirements and the amount of moderator needed to bring down the energy to thermal levels. The half-life of $^{252}Cf$ is 2.6 years.

Accelerator based neutron sources for TNA make use of either the D-D (deuteron-deuteron) reaction: $^2H+^2H\rightarrow^3He+n$, or the D-T (deuterium-tritium) reaction: $^2H+^3H\rightarrow^4He+n$. The deuteron (nucleus of the deuterium heavy isotope of hydrogen) is accelerated by a potential of 100-300 kV and the accelerated beam usually impacts a deuterated or tritiated target, such as titanium deuteride, or titanium triteride. The D-D reaction releases 3.26 MeV of energy and the D-T reaction releases 17.6 MeV of energy. Because the released energy is much larger than the beam energy, all outgoing neutrons leave with about the same energy, approximately 2.7 MeV for the D-D reaction, 14 MeV for the D-T reaction. A 1 mA beam of deuterons will produce about $10^9$ n/s for D-D reaction and $10^{11}$ n/s for the D-T reaction; somewhat smaller yields are produced from compact sealed-tube neutron generators. Because of the depletion of the target, sealed tube generators have operating life times of less than 2000 hours. As in the case of a radioactive source, the neutrons are produced isotropically and hence one can make use of only those neutrons that end up in the direction of the target to be inspected.

The gamma rays produced in TNA are usually detected with NaI(Tl) or BGO crystals. The gamma-ray spectrum usually consists of a full-energy photo peak plus two escape peaks plus a continuum Compton background. For the energies encountered in TNA and FNA (see below) typical sizes are 4"×4"×4" per crystal; while larger size crystals do exist, larger sizes result in higher count rates and in TNA could easily reach a MHz, which is probably the upper limit for single pulse counting with NaI. One then employs as many crystals around the package being inspected as geometry and cost allow.

Other scintillating crystals, such as BGO, have a higher efficiency than NaI, but have a lower energy resolution and a higher cost. Given the potential complexity of the gamma-ray spectra, the better energy resolution of NaI crystals favors their use.

Fast Neutron Analysis (FNA)

As in TNA, the detected radiation signaling the presence of an explosive is a gamma ray characteristic of one or more of its atomic components. The neutron interaction producing the gamma ray is, however, not thermal capture, but inelastic neutron scattering. In this process an energetic (i.e., fast, hence the name FNA) neutron collides with a nucleus and transfers some of its energy to that nucleus. The nucleus then decays back to lower excited states giving off one or more characteristic gamma rays. The minimum neutron energy needed to excite the first gamma-decaying state of $^{12}C$, $^{14}N$, and $^{16}O$ is 4.4 MeV, 2.3 Mev, and 6.2 MeV, respectively. One of the advantages of FNA over TNA is its sensitivity to $^{16}O$ and $^{12}C$, in addition to its sensitivity to $^{14}N$. This sensitivity comes about because the cross section for inelastic scattering from those atoms is much larger than the cross section for thermal neutron capture. For 14.8 MeV neutrons (i.e., those produced by the D-T reaction) the cross section to excite the above states is 200 mb for $^{12}C$, 70 mb for $^{14}N$, and 100 mb for $^{16}O$. However, since the minimum neutron energy needed to excite the oxygen is 6.2 MeV, one cannot use the radioactive source $^{252}Cf$ as the neutron source; one must use either the D-T reaction, which produces 14.8 MeV neutrons for an accelerator that provides the minimum of ~200 keV of energy to the accelerated deuteron, or the D-D reaction, with an accelerator that provides at least 5 MeV to the deuteron. (Other means of producing fast neutrons exist, but only the methods employed in machines produced purely for explosives detection using neutron-based technology are described herein.)

The gamma-ray detectors used in FNA are of the same type used in TNA, (mainly NaI) since the energies of interest are of the same order, with FNA perhaps affording the use of slightly smaller detectors since the maximum energy of interest (6.13 MeV from $^{16}O$) is smaller than that encountered in TNA (10.8 MeV from capture on $^{16}N$).

The improvement in FNA over TNA comes about because of the enhanced sensitivity to $^{16}O$, whose density is highly correlated with that of N in explosives (both O and N content is high in explosives). However, it is possible to get a false identification if it happens that there are two (or more) objects in the package being inspected one with high N content and the other with high O content, with the ratio being close to that of an explosive. To reduce the probability of such false positives, it is desirable to add imaging capability to the above techniques, i.e., is it is desirable to add the ability to localize the position of the N and O signatures within the package. The theoretical basis for variations of the FNA and TNA techniques, designed to add imaging capability and/or improve their sensitivity, is presented herein below.

Short Pulse FNA (SPFNA, also Known as Nanosecond Pulse FNA or Simply as PFNA).

This technique is based on FNA. The deuteron beam producing the neutrons through its interaction with a deuterium target is pulsed, i.e., the beam particles are bunched together (by electromagnetic means) into pulses each about 1 ns ($10^{-9}$ s) in duration and the pulses repeated about 1-5 MHZ, i.e., the time between one pulse and the next is about 200-1000 ns. The reason for this short pulsing is to determine where the neutron interacted in the package being inspected, and hence to localize the source of the gamma rays (and hence the source of the O and N). The localization along the direction of travel of the neutron is deduced as follows: the electronics that produce the deuteron pulse in the beam generate a fast time signal with each pulse. This time signal starts an electronic timer; when a gamma ray is detected in the NaI (say) the generated pulse is used to read the timer. (In practice the timer is started on the NaI signal and stopped on a delayed version of the beam pulse signal.) The measured time is linearly proportional to the distance traveled by the neutron and hence gives the position along the neutron travel direction where the scatterer is located. (The effect of the additional time taken by the gamma ray to travel from the neutron interaction site to the detector is discussed below.) The position in the two directions perpendicular to the neutron travel direction is determined by sufficient collimation of the neutron beam and by rasterizing the beam along one of the two directions (say the vertical direction) while a conveyor belt carrying the package being inspected and moving at a known speed rasterizes the object along the horizontal direction.

The position resolution (along the beam direction) is determined by the speed of the neutron, the duration of the pulse, and the time resolution of the NaI-electronics combination. For an 8.4-MeV neutron, the speed is 2.8 cm/ns; for a NaI detector the time resolution is at best 1 ns; when combined in a statistical way with the 1 ns pulse width the resulting time resolution is probably at best 1.4 ns, leading to a position resolution of about 2.8 cm/ns*1.4 ns=4.0 cm. (=1.6"). For a 14.8 MeV neutron, such as would be produced by a low-voltage D-T accelerator, the neutron speed is 3.7 cm/ns and the corresponding resolution would be 2.1". The resolution in the direction perpendicular to the beam direction is determined primarily by the collimation of the neutron beam and other geometrical considerations. Because of the much larger speed of gamma-rays (the speed of light=30 cm/ns), the additional time taken by the gamma ray to travel from the point of interaction to the detector is small compared to that taken by the neutron to travel within the package; nevertheless, with a knowledge of the position of the detector, its contribution can be taken into account with sufficient accuracy so as not to degrade the position resolution.

One factor contributing to the degradation in position resolution is scattering of the neutron prior to its gamma-registering interaction; the probability of that interaction depends on the size and content of the package being inspected.

Long Pulse FNA (LPFNA, Microsecond Pulse FNA or Gated FNA, or Gated FNA/TNA)

Like in SPFNA, the deuteron beam producing the neutrons is pulsed, however the pulse duration here is on the order of several microseconds (typically 10-50 µs), and the separation between pulses is on the order of 100-1000 µs. The reason for the pulsing here is not to obtain position information (the pulse duration and the resulting spread in interaction positions is far too large to provide useful imaging), but rather to improve the sensitivity and accuracy of the gamma-ray measurement. This is done by separating those gamma counts that arrive during the pulse (i.e., with the beam on), from those that arrive in between pulses (beam off). The former are then largely due to fast neutron interactions (i.e., close to what would be observed in an idealized FNA measurement), and the latter largely due to thermal neutron interactions (i.e., close to what would be observed in an idealized TNA measurement). In principle one can also employ a "pure" gated TNA technique (GTNA), in which the neutrons are thermalized with a moderator before they get to the package and then only count gammas during the beam off period. It should be clear that in either case, the pulsing is still too short to be done by mechanical means and hence only electronically generated neutrons (i.e., accelerator-based) can be used.

Neutron Resonance Attenuation (NRA)

In this technique a ns-pulsed beam of neutrons, with a broad energy spectrum (0.5-5 MeV) enters the package to be inspected from one side, and the neutrons that pass through the package are detected on the other side. The elements making up explosives (N, O, C, H) have large scattering cross sections at specific energies (that is resonances in the cross section) and hence, if present, would scatter away neutrons of that energy from the beam (i.e, the beam component at that energy would be attenuated). Therefore by looking for depletions in the transmitted neutron beam at characteristic energies the presence of explosives constituents could be deduced; the depth of the depletion provides a quantitative measure of the total areal density (density×thickness) of the scattering element along the beam direction. By rasterizing the beam (and/or the target), a two-dimensional shadowgram of the elements of interest can be formed. The neutron energy is usually measured with a Time-of-Flight (ToF) technique: the beam pulse starts a timer and the neutron detector pulse stops the timer. The measured ToF then gives information on the velocity of the neutron (and hence its energy), since the distance between the neutron source and the detector is fixed. The sensitivity of the technique depends, among other factors, on the energy resolution, which, in turn, depends on the length of the flight path, with longer flight paths giving higher resolution. Typical flight paths are 2-10 m long.

Associated Particle Imaging (API)

This technique uses the neutrons to interrogate the target in essentially the same way FNA does: a fast neutron excites the N, O and C nuclei and a subsequent gamma characteristic of these nuclei is detected. The imaging is done in a different way than in SPFNA, though. The reaction used to produce the neutron is the D-T reaction: $^2H+^3H\rightarrow^4He+n$. In this reaction the direction of the alpha particle (the nucleus of $^4H$) is correlated with the direction of the neutron (for the low beam energies typically used in the D-T reaction the alpha particle and the neutron are emitted essentially back-to-back). Therefore if the alpha particle is detected at a known direction (say by using a position sensitive detector and/or an array of detectors each with a small angular size) then the direction of the associated neutron is known. The position of the N, C, O along the (now known) direction of the neutron is obtained from the time difference between the alpha particle and the gamma ray.

While API would allow the use of a simpler accelerator than used in SPFNA, and would also allow a larger area of the target to be inspected at a time, the high count rates in the alpha detectors necessitate the use of lower beam currents and hence longer inspection times. While there may be ways to ameliorate the alpha count rate problem, for example by using a large number of small detectors each with a lower count rate, such systems have not, to our knowledge, been developed commercially yet.

Other Nuclear (Non-Neutron)—Based Bulk Explosives Detection Technologies

An overview of other nuclear-based techniques for explosives detection that do not rely on the generation and interaction of neutrons follows. The theoretical basis for two technologies that are under active commercial development, Gamma Resonance Technology (GRT) and Gamma Radiography, is presented herein below.

Gamma Resonance Technology (GRT)

As in Fast Neutron Analysis (FNA), GRT detects explosives by detecting the presence of one of the principal components of explosives, nitrogen. The nitrogen is detected by probing the package with a gamma ray whose energy is uniquely tuned to have an enhanced interaction probability with nitrogen. Further, the gamma-ray beam is produced in such a way that only nitrogen along a specified path interacts with the beam, thus allowing imaging of the nitrogen. The way these unique gamma rays are produced is as follows: A beam of protons with an energy of 1.75 MeV impinges on a $^{13}C$ target. Some of the protons are captured by the $^{13}C$ nuclei to form $^{14}N$ in an excited state at 9.172 MeV. About 5% of the time that excited state decays by emitting a gamma ray with an energy of 9.17 MeV (the remaining 95% of the time the state decays back into a proton plus a $^{13}C$ nucleus). Now the laws of physics, at the microscopic level, seem to be time reversible, so that if the process in which a stationary excited $^{14}$N nucleus decays to the ground state by emitting a 9.17 MeV ray happens, then its time inverse, namely the process in which a $^{14}$N nucleus in its ground state absorbs a 9.17 MeV gamma ray to become an excited $^{14}$N at 9.172 MeV excitation should also happen, with essentially equal probability. So the presence of $^{14}$N in the package being inspected can be inferred by monitoring the number of 9.17 MeV gamma rays passing through the package. A decrease in the number of transmitted gammas is indicative of the presence of $^{14}$N, potentially signaling the presence of an explosive. Now there is a slight complication in the physics which has both negative and positive consequences for explosives detection. The excited $^{14}$N produced by the beam is not stationary, but is moving in the direction of the beam (it has to carry the momentum brought in by the proton). Because of this motion, the gamma rays emitted in the forward direction (i.e., in the same direction as the proton beam) have more energy than can be absorbed by a nitrogen at "rest", while gamma rays emitted in the backward direction have less energy and cannot excite the $^{14}$N to the excited state at 9.172 MeV. Consequently, there is a specific angle (relative to the proton beam direction) at which the gamma rays have just the right energy to be absorbed by the $^{14}$N. This angle is about 80.5°.[2] The natural width of the 9.172 MeV level in $^{14}$N is 122 eV, so that gamma rays with about that much spread in energy can still be resonantly absorbed by the $^{14}$N; the spread in angle allowing that spread in energy is about 0.2°.

[2] At that angle the energy of the gamma ray emitted by the moving $^{14}$N is 9.175 MeV, about 3 keV higher than the excitation energy of the resonant state in $^{14}$N. This extra 3 keV is needed because upon absorption of the gamma ray the $^{14}$N recoils back and hence takes up 3 keV of the energy of the gamma ray.

The negative consequence to the fact that only gamma rays emitted within less than half a degree from a cone with half angle of 80.5° from the beam direction is that only a small fraction of the emitted gamma rays (about 0.4%) fall within that range. The positive consequence is that the narrow resonant fan beam of gammas can be used to image the nitrogen content of a package as it passes through the slice, without the need for very precise collimation of the gamma beam.

There are two ways the presence of $^{14}$N in the package under inspection can be deduced: 1) a decrease in the number of counts of 9.172-MeV gammas along the direction of the cone. To be sensitive to that decrease, a detector capable of discriminating between the resonant gammas and the non-resonant gammas is needed. The principle used is essentially the same one used in detecting the $^{14}$N: a detector with $^{14}$N content is used; some fraction of the transmitted resonant gammas will be resonantly absorbed by the $^{14}$N in the detector; the 1.75-MeV protons from the decay of the excited $^{14}$N to p+$^{13}$C are detected.

2) Detection of 9.1 MeV gammas resonantly scattered by the $^{14}$N away from the cone. Such a detector would be placed at relatively backward angles from the resonant gamma fan. The detector need only have moderate energy resolution for 9 MeV gammas, since the probability of non-resonant scattering is very small.

Gamma Radiography

Gamma Radiography employs exactly the same principle as x ray radiography: The variation in the absorption of a beam of photons as an object is scanned by the beam is used to from a shadowgram of the object. The shadowgram is produced because denser objects are more absorbing than less dense objects. In gamma radiography the gamma rays are produced by the decay of a radioactive isotope, instead of an x ray tube, or an electron accelerator. Typical sources used are $^{137}$Cs, which produces a 662-keV gamma ray, and $^{60}$Co, which produces two gamma rays, one at 1172 keV and the other 1332 keV. The higher energy of these gamma ray sources, compared to typical x ray sources, enables the examination of thicker targets; by the same token this higher penetration means that the contrast in the shadowgrams is relatively low.

Nuclear Quadrupole Resonance (NQR or QR)

Quadrupole resonance (QR, or more formally, nuclear quadrupole resonance, NQR) offers a highly specific method of detecting and identifying crystalline materials, including many explosives. Specially tuned pulses of radio waves in the 0.5-5 MHz range are applied to the sample. The radio waves are absorbed by nuclei of atoms in crystals within the sample and re-emitted a short time later. These weak re-emitted radio waves are detected by a sensor coil in the NQR receiver. The radio spectrum corresponds to particular atoms in a particular molecular structure, so each peak in the spectrum indicates a unique crystalline material.

Not all atomic nuclei respond to the QR radio pulses. The resonance effect is specific to nuclei with magnetic spin quantum numbers greater than or equal to 1, which includes Nitrogen-14 and other nuclei typically found in explosives. Another requirement for QR is that the nuclei must reside in an environment with a static or non-temporally averaged electric field gradient (EFG). What this means practically is that the nuclei must exist in an environment where the arrangement of surrounding charges remains fixed for at least a few microseconds. Nuclei in solid, amorphous materials could posses a QR spectrum, but that spectrum would tend to be broad and indistinct reflecting the presence of many different EFG environments. Nuclei in crystalline environments where atomic arrangements regularly repeat and the atoms don't move much will have narrower QR spectra as long the charge arrangement surrounding each nucleus gives a non-zero EFG. This describes the situation for many explosive and drug compounds. Nuclei in liquids do not possess a QR spectrum because the EFG is constantly changing and averages to zero much faster than 1 microsecond.

Although somewhat related to Magnetic Resonance Imaging used in medicine, QR is distinctly different in several ways. The most notable difference is that QR does not use a magnet to polarize the nuclei. QR polarization results from different energy states for the nuclei in the EFG. Not having to use a magnet is a major advantage of QR over competing techniques based on other magnetic resonance effects. Some of these advantages are lower cost, simpler design, and easier portability. The other difference between QR and MRI is that QR normally does not yield an image. A positive QR signal characteristic of an explosive indicates the presence of an explosive somewhere within the sample. Some degree of localization may be possible by taking advantage of the spatial distribution of RF field produced by specific antenna designs. Like MRI, QR uses RF radiation that is non-ionizing, so that it is generally safe for use on or near personnel.

The RF pulses are feed into a coil surrounding or adjacent to the sample, thereby producing RF fields within the sample. Likewise, the signal pickup coil must surround or be near the sample. In some cases, the transmit and receive coils are one in the same. Design of these coils as effective antennas for each NQR application and the associated electronics to handle and analyze the signals are major aspects of NQR technology development.

Because this technology uses radio frequency fields, RF shielding of the item under inspection becomes a possible means for defeat. Separate means can be devised to detect when an item being inspected contains a shielded region.

Trace Detection Technologies (a) Trace Detection Technologies Summary

Intrusion into the package is required to limit false negative objects, i.e. not seeing a well packaged explosive, to an acceptable level. Once intrusion into the package is acceptable Trace Detection Technologies are appropriate to identify specific chemical explosive and appropriate emergency response. The various trace detection technologies are described in the following sections.

(b) Trace Detection Technology Description

Trace Detection Technologies require physical transport of the sample (explosive) to the detector. Detectors only respond to (detect) gas phase chemical species. Particulate transported to a detector must go through a vaporization phase change prior to detection. Detection limits are best defined in absolute mass at the detector. Sampling, or transporting the chemical to the detector, is the most important limitation of trace technologies.

To illustrate the significance of packaging on detection explosive systems, two cases are described herein below.

The technology is adequately described by breaking the technology into three parts; sampling, sample preparation, and detection. The three independent parts are detailed in Table 1. First, define the analytical situation or problem, and then select one technique from each column appropriate to maximize and tailor the Trace Detection Technology to the problem.

TABLE 1

Trace Detection Technologies have three independent parts that are mixed and matched to achieve analytical goals

| Sampling Method | Sample Preparation | Detectors |
|---|---|---|
| Air, human plume | None or direct injection | Ion Mobility Spectrometer |
| Air, portal | Chromatography | Mass Spectrometer |
| Air w/absorbent preconcentration | Cryo-fractionating | Infrared spectrometer |
| Wipe sample | Thermal desorption | Electron Capture Detector (ECD) |

Example detector sensitivities are listed in Table 2. These are estimates based on ideal laboratory tests. Detector sensitivity is often compound (chemical functionality) specific. In real world applications, significantly worse detection limits should be expected. Much of the sensitivity lost by taking instrumentation out of the laboratory is regained through a pre-concentration step as part of the sampling. Little difference in sensitivity is seen as a discriminator between manufacturers at these levels of detection once installed in the field.

Mass spectrometers (MS) and infrared (IR) spectrometers are generally considered separately from other detectors as they provided chemical structural information. This additional dimension to the detector provides significant advantages over nonspecific detectors. Using MS and IR spectrometers, the explosive in the object can be identified.

TABLE 2

Detector Sensitivity Limits

| Detector Type | Lower Detection limit (gm) | Linear Range | Use |
|---|---|---|---|
| Nonspecific Detector Technologies | | | |
| Thermal Conductivity | $10^{-6}$ | $10^4$ | General |
| Flame Ionization | $10^{-10}$ | $10^6$ | Organic |

TABLE 2-continued

Detector Sensitivity Limits

| Detector Type | Lower Detection limit (gm) | Linear Range | Use |
|---|---|---|---|
| Electron Capture | $10^{-12}$ | $10^2$ | Variable |
| Chemiluminescence | $10^{-10}$ | $10^5$ | Oxides of nitrogen |
| Surface Acoustic Wave | $10^{-12}$ | $10^5$ | General |
| Cross-section Ionization | $20^{-6}$ | $10^5$ | General |
| Phosphorus | $10^{-11}$ | $10^4$ | Organo-P Compounds |
| A little better than Nonspecific | | | |
| Ion Mobility Spectrometry | $10^{-12}$ | $10^4$ | High Proton Affinity |
| Specific Detector Technologies | | | |
| Mass Spectrometer | $10^{-9}$ | $10^4$ | General |
| Infrared spectrometer | $10^{-9}$ | $10^4$ | General |

Ion Mobility Spectrometer (IMS) detector are one step up from a nonspecific detector. What is compromised in resolution is gained in speed, usability, weight and cost. Within limits IMS can be used to identify chemical species through the use of computational analysis.

Chromatography cannot be used as a stand-alone detector technology. It can be used with most detectors and functionally prepares the sample, separates chemical species to facilitate the use of nonspecific detectors, or simplify computational analysis of MS and IR detectors when complex mixtures are sampled.

These technologies, and specifically MS/RGA with a thermal sample inlet, are appropriate to use when the package can be intruded upon and the specific chemical explosive needs to be identified to guide an emergency response.

Mass Spectrometry

Mass spectrometer detectors fall into two types; bench units primarily used in laboratory settings and require highly skilled operators, and mobile units. Mobile units designed for gas analysis are often called RGAs (residual gas analyzers), and are often equipped with a thermal sample inlet. The sample inlet serves two (2) functions. First, sample is drawn into the sample inlet cold to concentrate chemical species and thus increase sensitivity. Second, the inlet is quickly heated vaporizing collected chemical species for introduction to the mass spectrometer detector allowing measurement of a variety of low vapor pressure chemical species at higher sensitivity.

The mass spectrometer detector has an electron ionization (about 70eV) source. As chemical species enter the ionization beam positive ions form. The mass to charge ration of these ions and the uni-molecular decomposition, or fragmentation, products are measured. Every molecule has a unique mass fragmentation pattern that can be used to separate and identify it from any other compound. Greater computing power is needed when either more components are in the sample mixture or the more unknown chemical species are in the sample. To lessen the required computing power chemical species are separated or fractioned through the use of a short chromatographic column placed between the thermal inlet and the detector.

Mass spectrometer detectors greatest strength lies in its ability to provide structural proof of the chemical species.

When screening level gets down to the point where chemical speciation is required (specific explosive or drug), this is the technology to use.

Ion Mobility Spectrometer (IMS)

IMS is well developed and in various forms has been around for years. Samplings offered by the listed IMS venders are air flow (human plumb or portals) or wipe, sample preparation is direct injection and detection is by IMS using atmospheric pressure chemical ionization (APCI).

IMS sensitivity is dependent upon the chemical species, generally proportional to higher proton affinity, and can range over several orders of magnitude ($10^{-12}$ gm to $10^-$gm).

Ion mobility spectrometers use a radioactive source (about 15 milli-curies Ni63, some use Am241) to ionize gas molecules at atmospheric pressure (APCI atmospheric pressure chemical ionization). Ion clusters form and drift in a field, drift tube, being detected as they collide with spaced detector elements along the tube. The time of drift (mobility) is roughly a measure of the cluster mass. Often referred to as a time-of-flight measurement. Its limited chemical speciation is achieved based on the drift time or mobility in a positive and/or negative field. This is very oversimplified. The point is that IMS provides rudimentary identification of chemical species giving it advantage over a parallel technology, electron captor (ECD). It gives significantly less identification capability when compared to mass spectrometry (MS). Most drugs and explosives have high proton affinity supporting IMS high detection sensitivities to these classes of compounds.

Electron Capture Detector

Electron capture detector (ECD) is a nonspecific detector. ECD use a radioactive beta source to ionize a gas inside a cell. The current at the collector electrode is measured. As chemical species inter the cell they react with the ionized gas decreasing current flow to the detector. As ECD is very sensitive to electronegative chemical compounds and very insensitive to neutral compounds it is considered a selective nonspecific detector.

Chemiluminescence

The Chemiluninescence detector, although specific for oxides of nitrogen, is considered a general nonspecific detector with high sensitivity.

A detector technology generally used to measure the concentration of oxides of nitrogen (NOx). "Nitrogen oxide (NO) and ozone (O3) react to produce a characteristic luminescence with an intensity linearly proportional to the nitrogen oxide concentration", Model 42c Instruction Manual, Thermo Environmental Instruments. Nitrogen dioxide is first reduced by passing over a hot catalyst followed by mixing with ozone. Some additional specificity is achieved by adjusting the catalyst and the catalyst temperature. Chemical species with high nitrogen content will react. Some explosives, energetic materials, and drugs react similarly when reacted with ozone either before or after the reduction catalyst.

Olfaction

Technologies offered under the Olfaction name are more a way of handling data than a specific detector. An array of very small simple materials that differ in chemical properties (i.e. solubility or polarity) will interact or react with a specific chemical species (TNT or cocaine or anthrax) differentially exhibiting a unique response pattern. The more elements in the array the more unique the pattern. Thirty-two elements are common. Chemical identification is correlated to the patterned response. The marketing term used often is "pattern recognition". It can be a very powerful tool.

In some cases an array of polymers that differ in physically properties, primarily solubility is used. The properties are measured electrically, change in resistance. The detector is about the size of a stamp. In other cases, an array of metal porphyrins is used. The pattern that develops upon exposure is read optically. Both of these cases require pattern recognition algorithms for chemical identification.

Frequency Modulated Infrared Spectroscopy (FMIRS)

Infrared spectroscopy is a group of techniques that measure the energy absorbed through molecular bond vibration and molecular rotation. Every chemical species has a unique IR fingerprint. The significance of these techniques is that chemical structural information is measured positively identifying the chemical when vibrational energies are collected over sufficient range. IR and MS are the two techniques under this heading that provide positive specific chemical identification. The sensitivity is proportional to the number of molecules that interact with the energy source. The number of interactions is increased by increasing the distance the energy source travels through the sample.

FMIRS is not a standard acronym in IR spectroscopy. There are a number of techniques in IR spectroscopy that use frequency or amplitude modulation.

Biotechnology

Microbiologists and geneticists have made great strides genetically engineering microbes that can specifically interact with chemical species, explosives, drugs, viruses, etc. The interaction results in some change in physical property of the supported microbe that can be measured. Most elegant of these is bioluminescence, biological light, emitted proportional to the interaction. Sufficient specificity is often attained for chemical characterization. A microbe must be developed for each chemical species of interest.

Surface Acoustic Wave Resonator (SAW)

A SAW detector is a crystal resonator held isothermal. A sample is passed over the detector. As chemical species in the air passing over the detector, they condense resulting in a change in resonator frequency. The amount of shift is a function of the number or concentration of chemical species in the air above the resonator.

SUMMARY OF THE INVENTION

The present invention provides methods for interconnecting sub-systems, where each sub-system utilizes a single technology, and for identifying combinations of multiple technologies, where the combinations have a figure of merit satisfying a given criterion.

In one embodiment, the method of this invention for detecting the presence of a characteristic in an object includes:

(a) providing two or more detection sub-systems, (b) establishing a plurality of decision rules, to arbitrate between results of detection technologies and to detect the presence of the characteristic in the object, (c) first determining, utilizing one of the three or more detection sub-systems (detection technologies), whether the characteristic is present in the object whether the characteristic is present in the object, (d) repeating step (c) until all provided technologies have been utilized;

(e) finally determining, utilizing said plurality of decision rules, whether the characteristic is present in the object.

Systems implementing the above methods are also disclosed.

For a better understanding of the present invention, together with other and further objects thereof, reference is made to the accompanying drawings and detailed description, and its scope will be pointed out in the appended claims.

BRIEF DESCRIPTION OF THE DRAWINGS

FIG. 3 illustrates the Probabilities set for the subsystem of FIG. 2;

DETAILED DESCRIPTION OF THE EMBODIMENTS OF THE INVENTION

The methods and systems of the present invention implement interconnected systems for detecting a presence of a characteristic in an object. It should be noted that "object" as used herein refers to the situation in which the characteristic is being detected. An "object" as used herein below may be, but is not limited to, an object, a patient, a region or location on a body, an object at a time and place, or the interior of an object. A "characteristic" as used herein refers to that which is being detected. A "characteristic" as used herein below may be, but is not limited to, an undesired substance (such as, but is not limited to, an explosive) within an object, whether an undesired substance is not present in an object, a particular disease at a location in a patient, location of targets, obstacles and objects in an area or volume.

Strategies for interconnecting sub-systems, each sub-system utilizing a single detection method, and for selecting combinations of sub-systems designed according to one of the simpler strategies are disclosed hereinbelow.

Figure 1:
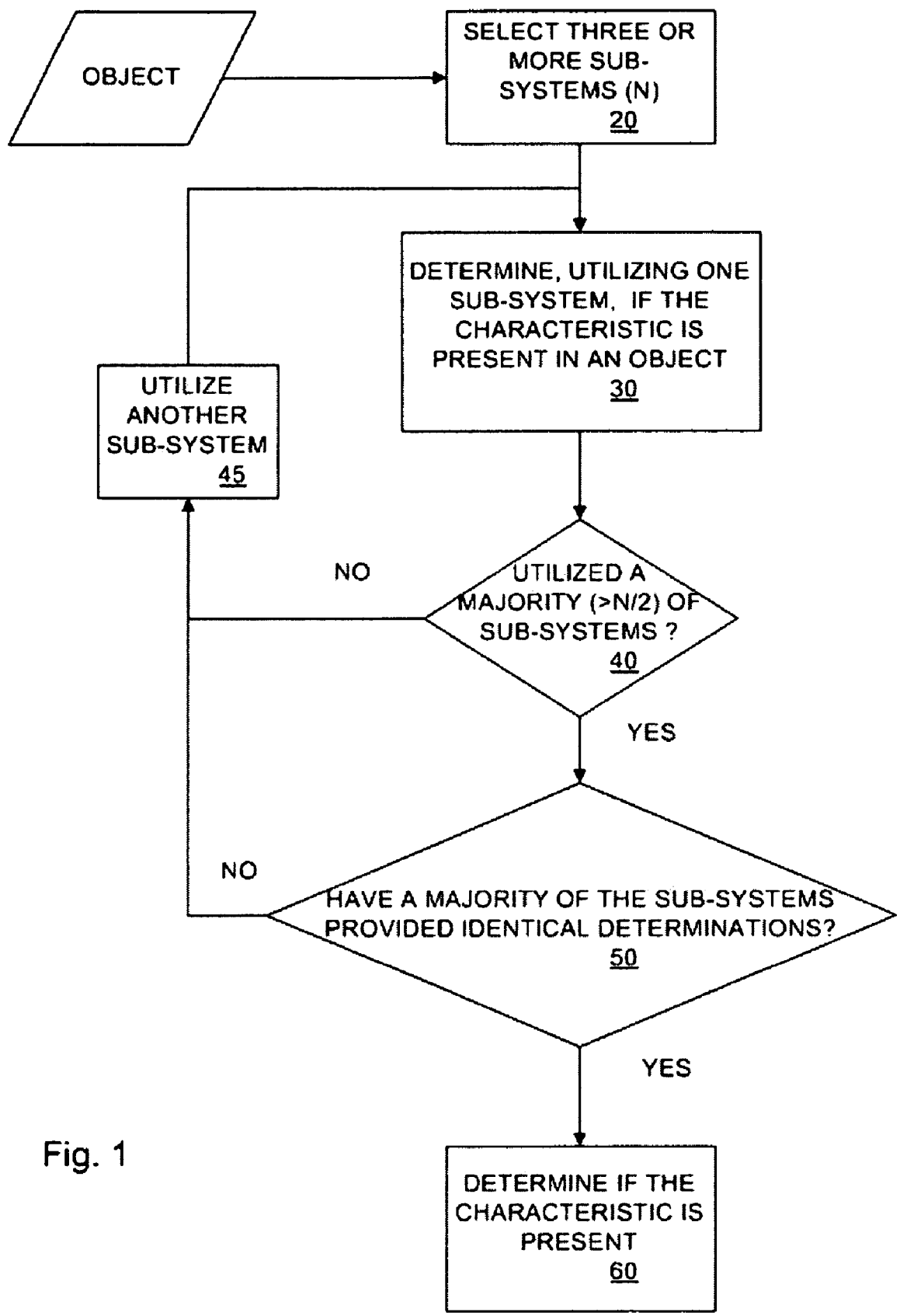
FIG. 1 depicts a flowchart of an embodiment of a method of this invention.

FIG. 1 depicts a flowchart of an embodiment of a method of this invention. Referring to FIG. 1, three or more detection (N) sub-systems are provided (step 20, FIG. 1). The first sub-system is utilized to determine whether the characteristic is present in the object or the characteristic is absent in the object (step 30, FIG. 1). Subsequent sub-systems, up to the last sub-system, are utilized to determine whether the characteristic is present in the object (steps 30, 40, FIG. 1). After a majority of objects (>N/2) of the sub-systems have been utilized to determine whether the characteristic is present, if previous determinations for a majority of the three or more detection sub-systems are not identical, another subsystem is utilized to determine whether the characteristic is present in the object(step 50, FIG. 1). The process continues until determinations for a majority (>N/2) of the three or more detection sub-systems are identical or until all sub-systems have been utilized (step 55, FIG. 1). If identical determinations for a majority (>N/2) of the three or more detection sub-systems are obtained, a final determination of the presence of the characteristic is obtained (step 60, FIG. 1). If a majority of identical determinations are not obtained and all sub-systems have been utilized (as, for example, in an embodiment utilizing an even number of sub-systems), the final determination of the presence of the characteristic is obtained utilizing a pre-determined criterion.

Figure 2:
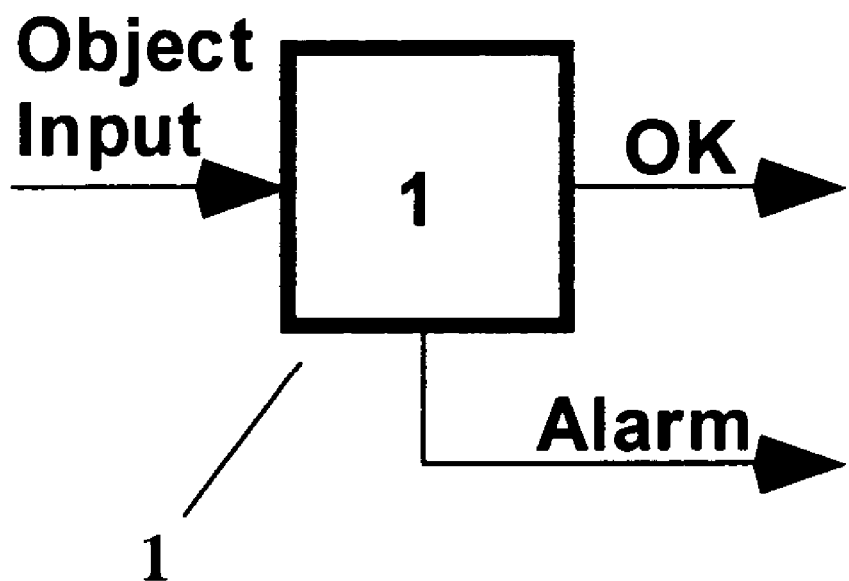
FIG. 2 depicts a Block/Flow diagram for a subsystem for determining the presence of a characteristic in an object.

A detection technology can be represented by the flow diagram in FIG. 2. Referring to FIG. 2, when an object is examined, subsystem 1 produces an Alarm or OK response if the object does or does not contain a given characteristic, respectively. The probabilities of correct responses and errors are shown in FIG. 3.

Referring to FIG. 3, PD, the probability of detection, is the probability of detecting a characteristic if there is a characteristic present. PFA, the probability of false alarm, is the probability of detecting a characteristic, if there is none. This leads to threat mitigation procedures.

Referring again to FIG. 3, 1-PD is the probability of failing to detect a characteristic. In the case where the characteristic is an explosive, a failure to detect, when there is an explosive present, could lead to an explosion.

If PFA is high it leads to costly time consuming threat mitigation procedures. If PD is low and 1-PD is high this could lead to failure to detect the characteristic. In the case where the characteristic is an explosive, a failure to detect could lead to an explosion, loss of life, and extreme costs. Note that PD and PFA do not have to add to 1. Tuning any single system (or technology) tends to raise or lower both PD and PFA, together.

Combinations of technologies can be considered to raise the system probability of detection (SPD) and lower the system probability of false alarm (SPFA), but not all strategies produce improvements. Multi-technology systems require independent technologies in the subsystems.

Figure 4:
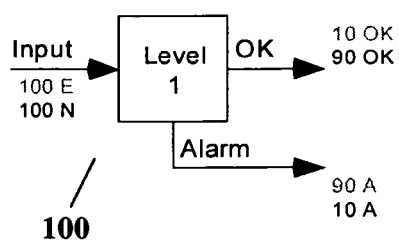
FIG. 4 depicts a Block/Flow diagram for a Level 1 system (Assuming all levels have PD=90% and PFA=10%)
Figure 5:
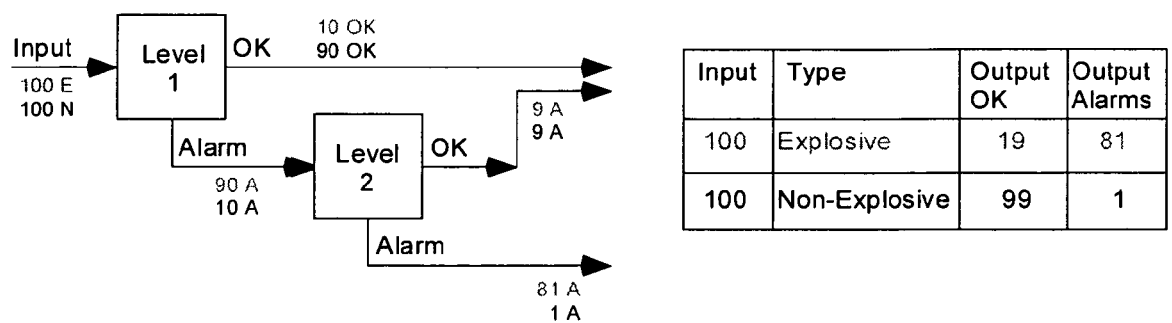
FIG. 5 depicts a Block/Flow diagram for a Level 2 system (Assuming all levels have PD=90% and PFA=10%)
Figure 6:
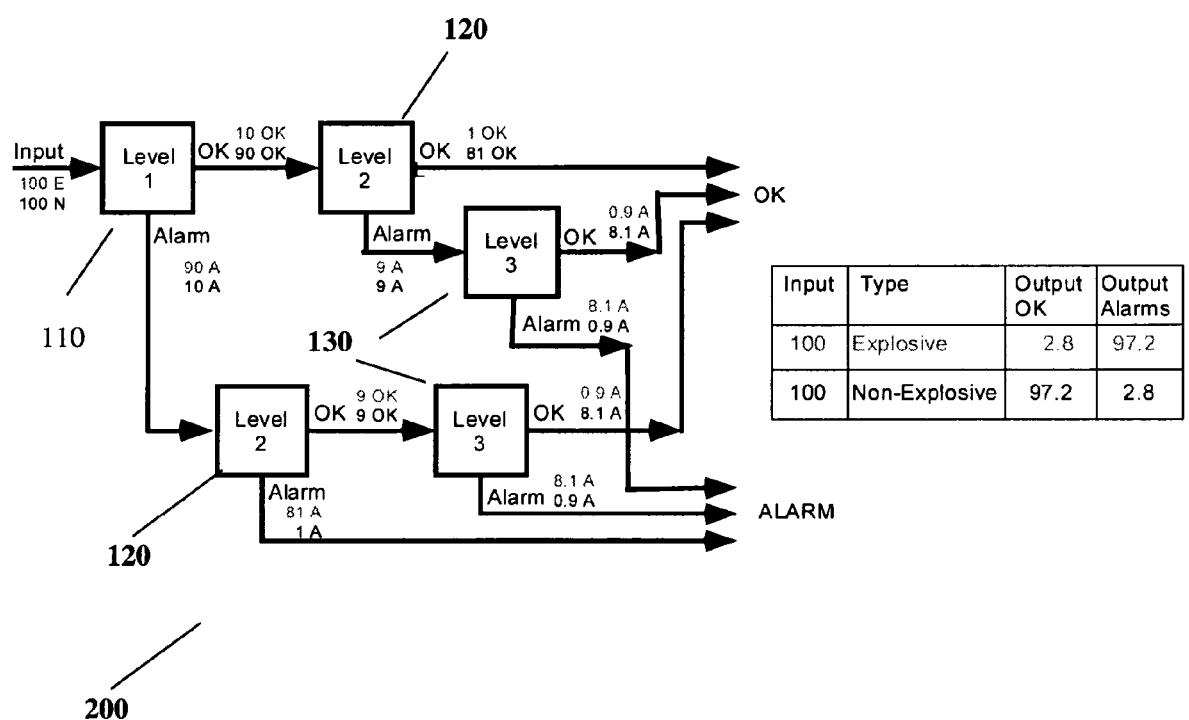
FIG. 6 depicts a Block/Flow diagram for an embodiment of a system of this invention (Assuming all levels have PD=90% and PFA=10%)

The following example strategies for a Level 1 System, a Level 2 Alarm Mitigation System, three level decision system, and the majority system assume PD=90% and PFA=10% for all technologies. FIGS. 4-6 show the result of examining 100 objects known not to have the characteristic (without explosives, for example) and 100 objects containing the characteristic (with explosives, for example). The System Probability of Detection (SPD) and the System Probability of false alarm (SPFA) can be calculated.

The Level 1 System 100, shown in FIG. 4, has a baseline SPD=90% and a baseline SPFA=10%.

FIG. 5 shows a 2 level Alarm Mitigation System strategy. The combined system improved the SPFA to 1% at the expense of significantly reducing SPD to 81%.

FIG. 6 shows a 3 level Majority System strategy. The system 200 is structured to require either two or three technologies to determine that the characteristic is not present ("OK the object") or two of three technologies to Alarm the object before a determination is made. The strategy is effectively having each the technologies vote, and the third level technology is used as the tiebreaker. In practice, the level 2 and level 3 technologies would probably be slower than the level 1 technology. The system could actually derive a significant speed-up using a state variable scheduler to direct objects to the least busy level. This is the only strategy that can improve both the SPD and SPFA at the same time and can improve the throughput.

In one embodiment, where only three detection techniques (sub-systems) are utilized, the probability of detection ($P_{D1}$) of the sub-system that has the highest probability of detection (110, FIG. 6) satisfies the following relation:

$$(1 - P_{D1}) \geq [(1 - P_{D1})(1 - P_{D2}) +$$
$$(1 - P_{D1})P_{D2}(1 - P_{D3}) + P_{D1}(1 - P_{D2})(1 - P_{D3})],$$

where $P_{D2}$ is a probability of detection of a second detection sub-system (120, FIG. 6), $P_{D3}$ is a probability of detection of a third detection sub-system (130, FIG. 6).

In another embodiment, the probability of false alarm ($P_{FA1}$) of the sub-system (also known as the probability of false positives) that has the lowest probability of false alarm (in one embodiment, 110, FIG. 6) satisfies the following relation:

$$P_{FA1} \geq [(P_{FA1})(P_{FA2}) +$$
$$(1 - P_{FA1})(P_{FA2})(P_{FA3}) + (P_{FA1})(1 - P_{FA2})(P_{FA3})] \text{ where,}$$

$P_{FA2}$ is a probability of false alarm of a second detection sub-system (120, FIG. 6), and $P_{FA3}$ is a probability of false alarm of a third detection sub-system (130, FIG. 6).

Embodiments in which both of the above conditions are satisfied by the same sub-system are also possible.

In the above embodiments, the probability of detection for the system and the combined probability of false alarm for the system are jointly improved over that of a single detection method (technology). It should be noted that the above described conditions can be met if all sub-systems (technologies) have the same probability of detection and the same probability of false alarm and the probability of detection is greater than 0.5 and the probability of false alarm is less than 0.5. It should also be noted that the sub-system that has the highest probability of detection is not, in every embodiment, the same sub-system that has the lowest probability of false alarm. It should be further noted that although, in the embodiment in which the same sub-system has the highest probability of detection and the lowest probability of false alarm shown in FIG. 6, although that sub-system is shown as the first sub-system in FIG. 6, the sub-system that has the highest probability of detection and/or the sub-system that has the lowest probability of false alarm could be placed in a different order (it could be, but not limited to, the second sub-system).

In another embodiment, the number of detection sub-systems is an even number. In that embodiment, a predetermined criterion is utilized to detect the presence of the characteristic. If a majority (>N/2) of identical determinations is obtained, the presence of the characteristic is detected. One embodiment of the predetermined criterion is, if a majority (>N/2) of identical determinations is not obtained, detecting the presence of the characteristic if half of the detection sub-systems determine that the characteristic is present.

In the embodiment in which the detection of the presence of a characteristic in an object is the detection of explosives inside objects, each one of the detection sub-systems (110, 120, 130, FIG. 6) can utilize, but is not limited to, one of the following technologies: X-ray technologies, Neutron-Based Bulk Explosives Detection Technologies, Nuclear non-neutron based Bulk Explosive Technologies, Nuclear Quadrupole Resonance Technologies, and Trace Detection Technologies. The Nuclear non-neutron based Bulk Explosive Technologies include Gamma Resonance Technology (GRT) and Gamma Radiography. It should be noted that other technologies (such as future technologies) can be utilized if available.

The Majority Strategy described above (and in FIG. 6) can be used to predict the functionality of technology combinations. The probability of detection and probability of false alarm represent a base line for combined technology systems. However, for a large number of sub-systems or for detecting presence of more than one characteristic in an object, other methods can be used. The Monte Carlo method can be used to determine the probability of detection or false alarm for any combination of sub-systems and for detecting presence of more than one characteristic in an object. The Monte Carlo method is a computational technique that uses random numbers to simulate the behavior of a system. By conducting a large number of simulation objects, properties of the system, which would not be obtainable by derivation from closed form mathematical solution, can be ascertained. An example, but not limited to, of detecting the presence of more than one characteristic in an object is the detecting of several particular explosives.

Figure 7:
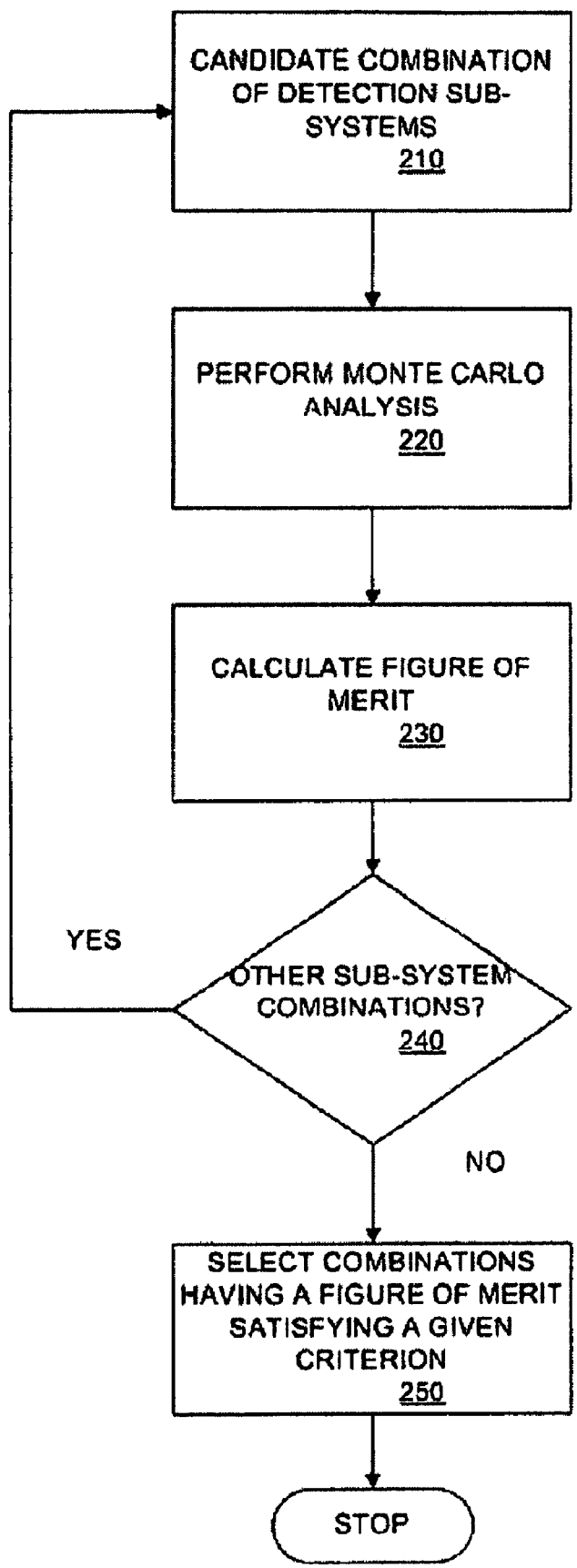
FIG. 7 depicts a flowchart of another embodiment of the method of this invention.

A flowchart of an embodiment of the method of this invention utilizing the Monte Carlo method is shown in FIG. 7. Referring to FIG. 7, a candidate combination including two or more detection sub-systems is selected (step 210, FIG. 7). A Monte Carlo analysis of detecting the presence of the one or more characteristics in the object for the system including the two or more detection sub-systems is performed (step 220, FIG. 7). Utilizing the results of the Monte Carlo analysis and system properties, a pre-defined figure of merit (also referred to herein below as a "cost") is calculated (step 230, FIG. 7). If other sub-system combinations are available for analysis, the previous steps are repeated (step 240, FIG. 7). Those combinations having a Figure of Merit satisfying a pre-determined criterion (in one embodiment, larger than a given value) are selected (step 250, FIG. 7).

In one embodiment, three sub-systems are selected utilizing the 3 level Majority System strategy of FIG. 6. In a particular embodiment of the Majority System strategy, the probability of detection ($P_{D1}$) of the sub-system that has the highest probability of detection (110, FIG. 6) satisfies the following relation:

$$(1 - P_{D1}) \geq [(1 - P_{D1})(1 - P_{D2}) +$$
$$(1 - P_{D1})P_{D2}(1 - P_{D3}) + P_{D1}(1 - P_{D2})(1 - P_{D3})] \text{ where,}$$

$P_{D2}$ is a probability of detection of a second detection sub-system (120, FIG. 6), $P_{D3}$ is a probability of detection of a third detection sub-system (130, FIG. 6).

In another embodiment, the probability of false alarm ($P_{FA1}$) of the sub-system that has the lowest probability of false alarm (in one embodiment, 110, FIG. 6) satisfies the following relation:

$$P_{FA1} \geq [(P_{FA1})(P_{FA2}) + (1 - P_{FA1})(P_{FA2})(P_{FA3}) + (P_{FA1})(1 - P_{FA2})(P_{FA3})] \text{ where,}$$

$P_{FA2}$ is a probability of false alarm of a second detection sub-system (120, FIG. 6), and $P_{FA3}$ is a probability of false alarm of a third detection sub-system (130, FIG. 6).

Embodiments in which both of the above conditions are satisfied by the same sub-system are also possible.

An embodiment of the method of this invention, utilizing the Monte Carlo method, for performing design trade-offs, selecting candidate sub-systems according to a pre-defined cost function (Figure of Merit) where the detection of the presence of a characteristic in an object is the detection of explosives inside objects is described herein below.

Referring again to FIG. 5, assume further that a probability of an explosive being present (PE) in 1 out of 100,000,000 objects or $10^{-8}$ and a probability of non-explosives being in the balance of the objects (PNE) of 0.99999999%.

The cost component (CC) consists of the sum of the cost of failure to detect an explosive and the cost of false alarms. Multiplying each of these by the cost of the response and the number of objects per year gives the expected system costs component per year. Equation 1 gives the cost component per year.

$$CC = (N*PE*(1-SPD)*CE) + (N*PNE*SPFA*CFA) \quad \text{Eq. 1.}$$

where CC is the system cost component, $/year; N is the number of objects per year being screened; SPD is the system probability of detection; CE is the cost of an explosive not being detected, $/object; SPFA is the system probability of false alarm; and CFA is the cost of a bomb squad examining a false alarm, $/object.

If it is assumed that the cost of an explosion is $1,000,000,000, the cost for a bomb squad handling a false alarm is $1,000, and the number of screenings is 100,000,000 objects per year, then expected cost component, CC, is $$CC = \$1,200,000,000/\text{year} \quad \text{Eq. 2.}$$

It may be possible to optimize the component cost, CC by examining the derivative of CC with respect to SPD and SPFA.

Other cost components include, but are not limited to, purchase price, installation, maintenance, operating cost.

In the embodiment of the application of the method of this invention to selecting candidate combinations of sub-systems for an Explosive Detection System (EDS) presented below, scoring criteria was utilized before applying the method of this invention and a ranking of individual EDS sub-systems was performed utilizing the scoring criteria prior to applying the method of this invention. Although the scoring criteria and the preliminary ranking are not necessary to perform the method of this invention, the scoring criteria and the preliminary ranking are described below since reference is made to them in the embodiment of the application of the method of this invention disclosed herein below.

EDS Scoring Criteria

The Evaluation Criteria used in the study are: Probability of Detection, Specificity, Probability of False Alarm, Unit Cost, Annual Maintenance Cost, Staff Requirements, Availability to Market, Footprint area, Weight, Throughput, Automation level and Defeat Immunity.

The Scoring Criteria, which establish scores based on evaluation criteria performance and corresponding weighting Factors, which establish the relative importance of Evaluation Criteria are shown in Table 3.

TABLE 3

EDS Scoring Criteria of this invention
EDS Scoring Criteria

| | Rank | | | | | |
|---|---|---|---|---|---|---|
| | Best | | | | | Worst |
| | Score | | | | | |
| Evaluation Criteria | 10 | 9 | 8 | 7 | 6 | 5 |
| Prob. Of Detection, % | >99 | 99-98 | 98-97 | 97-95 | 95-90 | 90-85 |
| Specificity (number of material parameters measured) | 5 or more | 4 | 3 | 2 | 1 | 1 |
| Prob. Of False Positive, % | <0.1 | 0.1-0.2 | 0.2-0.3 | 0.3-0.5 | 0.5-1 | 1-5 |
| Unit Cost, $K | <200 | 200-500 | 500-800 | 800-1000 | 1000-1200 | 1200-1500 |
| Annual Maintenance Cost, $K | <20 | 20-50 | 50-80 | 80-100 | 100-120 | 120-150 |
| Annual Operational Support, Full Time Equivalent Staff | 0 | 0.5 | 1 | 1.5 | 2 | 2.5 |
| Availability to Market, months | Now | 1-6 | 6-12 | 12-24 | 24-36 | |
| Footprint, Sq.-Ft. | <50 | 50-100 | 100-200 | 200-500 | 500-1000 | 1000-1500 |
| Total Weight, lb | <500 | 500-1000 | 1000-1500 | 1500-2000 | 2000-5000 | 5000-10000 |
| Throughput (objects/min) | >25 | 25-15 | 15-5 | 5-1 | N/A | N/A |
| Automation | Auto level 1 and 2 | Auto level 1 and manual level 2 | Auto level 1 | Manual level 1 | N/A | N/A |
| Defeat Immunity | Can't be defeated | Defeatable by expert, indicates defeated | Defeatable easily and indicates defeated | Defeatable and does not indicate defeated. | N/A | N/A |

TABLE 3-continued

EDS Scoring Criteria of this invention
EDS Scoring Criteria

| Evaluation Criteria | Rank Score 4 | 3 | 2 | 1 | Weight Factor note 10 |
|---|---|---|---|---|---|
| Prob. Of Detection, % | 85-80 | 80-75 | 75-70 | <70 | 20 |
| Specificity (number of material parameters measured) | 1 | 1 | 1 | 1 | 14 |
| Prob. Of False Positive, % | 5-10 | 10-20 | 20-30 | >30 | 14 |
| Unit Cost, $K | 1500-2000 | 2000-3000 | 3000-5000 | >5000 | 13 |
| Annual Maintenance Cost, $K | 150-200 | 200-300 | 300-500 | >500 | 2 |
| Annual Operational Support, Full Time Equivalent Staff | 3 | 4 | 5 | >5 | 2 |
| Availability to Market, months | | | | | 10 |
| Footprint, Sq.-Ft. | 1500-2000 | 2000-2500 | 2500-3000 | >3000 | 6 |
| Total Weight, lb | 10000-15000 | 5000-2000 | 20000-25000 | >25000 | 3 |
| Throughput (objects/min) | N/A | N/A | N/A | N/A | 3 |
| Automation | N/A | N/A | N/A | N/A | 1 |
| Defeat Immunity | N/A | N/A | N/A | N/A | 10 |

EDS Scores

Scores can be obtained for various explosive detection sub-systems (EDS). The characteristics of each EDS, recorded on an EDS Analysis Factors Form, are the basis for the scores.

The Figure of Merit is the sum of the products of the scores multiplied by the corresponding weighting factor, all divided by 100. An example of an EDS Ranking is shown below in Table 4.

TABLE 4

EDS Ranking of this invention
EDS Scores

| Technology | DECT | Fixed Emitter/ Detector | Diff Xray 1 | Diff Xray 2 | Diff Xray 3 | Side Scan Xray | Fixed Emitter/ Detector | LPFNA 1 | SPFNA | LPFNA 2 | TNA | NQR 1 | NQR 2 |
|---|---|---|---|---|---|---|---|---|---|---|---|---|---|
| Prob. of Detection | 3 | 2 | 4 | 3 | 4 | 2 | 2 | 4 | 4 | 3 | 3 | 3 | 3 |
| Specificity, note 5 | 3 | 3 | 4 | 4 | 4 | 3 | 3 | 3 | 4 | 3 | 1 | 4 | 4 |
| Prob. of False Positive | 3 | 2 | 4 | 4 | 4 | 2 | 2 | 4 | 4 | 4 | 3 | 4 | 4 |
| Unit Cost | 2 | 2 | 2 | 2 | 1 | 3 | 2 | 3 | 1 | 2 | 3 | 4 | 4 |
| Annual Maint. Cost | 4 | 1 | 1 | 1 | 1 | 2 | 2 | 3 | 1 | 3 | 4 | 4 | 4 |
| Annual Operational Support | 3 | 3 | 4 | 4 | 4 | 3 | 3 | 4 | 4 | 4 | 4 | 4 | 4 |
| Availability to Market | 2 | 3 | 3 | 2 | 2 | 1 | 1 | 2 | 4 | 1 | 3 | 2 | 2 |
| Footprint | 3 | 3 | 3 | 3 | 2 | 4 | 3 | 2 | 1 | 2 | 3 | 4 | 4 |
| Total Weight | 1 | 1 | 1 | 1 | 1 | 3 | 1 | 1 | 1 | 2 | 2 | 3 | 3 |
| Throughput, objects/minute | 3 | 4 | 1 | 2 | 1 | 2 | 4 | 2 | 3 | 1 | 1 | 2 | 1 |
| Automation Level | 3 | 3 | 2 | 2 | 2 | 3 | 3 | 2 | 4 | 2 | 2 | 2 | 2 |
| Defeat Immunity | 3 | 3 | 1 | 1 | 1 | 3 | 3 | 4 | 4 | 4 | 4 | 1 | 1 |
| Figure of Merit (note 11) = | 2.67 | 2.4 | 2.94 | 2.67 | 2.65 | 2.41 | 2.22 | 3.14 | 3.17 | 2.71 | 2.7 | 3.11 | 3.08 |
| notes | | | 4 | 4, 8 | 4, 8, 12 | 8, 9 | | | | | 4 | 4, 6, 7 |

NOTES:
1. Objects = tubs with flats 18" × 13" × 11" H, sacks with objects 40" × 30" flat or 36" L × 24" D, Outliers < 107" L.
2. Total Weight includes device + shielding (if applicable)
3. Floor space is the foot print area including shielding, square feet
4. Detect crystals only, therefore may not detect dynamite.
5. Specificity scoring: whole object at once = 0 pt; 2 D = 1 pt; 3 D = 1 pt; density = 1 pt; eff Z = 1 pt; linear x-ray attenuation coefficient = 1 pt; measure N = 2 pt; measure O, H, C = 2 pt; molecular 1 D = 1 pt; all scores are additive.
6. Based on TSA and FAA test estimates.
7. Aluminum foil will defeat NQR.
8. Ge detector requires LN or cooling. Can see crystals only so can't see Dynamite.
9. The Weight Factors total 100%.
10. The Figure of Merit is the sum of each score multiplied by the weighting factor, all divided by 100. The Best is 4 and the worst is 1.
11. This price based on unit cost. No quantity purchase data available.
12. Operational Support is on a basis of one shift per day.

The EDS Ranking is useful for comparing the individual explosive detection systems over a wide range of evaluation criteria.

A Composite Systems Comparison was performed utilizing the method of this invention for selecting candidate combinations of sub-systems as shown in FIG. 7. The Composite Systems Comparison identifies which of the EDS sub-systems produce combined systems in which the Figure of Merit indicates that the performance is above a given performance value and the "cost" is below a given "cost" value (with a goal of the best performance for the lowest cost). The input data are the values from the Analysis Sheets or the midrange of the EDS Ranking. Technologies that cannot detect noncrystalline (NC) materials are assumed to have a PD NC of 30%.

The EDS sub-systems from the EDS Ranking study are combined in groups of one, two, and three, using the Majority Strategy described herein above. Each combination is analyzed by using a Monte Carlo simulation to determine its performance. The Monte Carlo analysis interprets a random numbers generator to determine if the object being screened is:

Does not contain an explosive
Contains a crystalline explosive
Contains a noncrystalline explosive Some of the technologies do not detect noncrystalline explosives well. Thus, separate probabilities of detection are used as inputs to the calculations. Actual data on how much crystalline and noncrystalline explosive are present in objects is not known. The Bureau of Alcohol, Firearms, and Tobacco (ATF) website reports that 86% of the explosives stolen each year are crystalline explosives (dynamite). Detecting an explosive as common as dynamite should be an important consideration.

The Monte Carlo analysis outputs are:
(a) PD NC Probability of detection for noncrystalline materials. The value is from the Analysis Sheet or the midrange of the EDS Ranking. The value used was assumed to be 30% for technologies that cannot detect noncrystalline materials
(b) PD C Probability of detection for crystalline materials.
(c) SPD Probability of detection for the combined system.
(d) Specificity Combines the specificity of all input technologies.
(e) SPFA Probability of false alarm for the combined system. Unit Cost Adds the cost of all combined sub-system.
(a) Maintenance Cost adds the maintenance cost of all combined sub-systems.
(b) Staff Adds the number of full time people required for each subsystem per shift.
(c) Availability Months until availability to the market.
(d) Floor Space Adds the area required for each subsystem.
(e) Weight Adds the weight of each subsystem.
(f) Throughput Adds the time required for each subsystem to screen the object.
(g) Automation Combines the automation levels for each subsystem.

CFOM Cost Figure of Merit. (See below.)

The CFOM was derived by calculating the actual cost per year for each combination of sub-systems, using the equation:

$$CFOM = 120*(1-PD) + 120*PFA + \text{unit cost} + \text{maint. Cost} + \text{staff cost (all in \$ millions)}$$

This equation was derived by estimating that the cost for an explosive detection error to be $120 M/year times the probability of a missed detection and the cost of false alarms is $120 M/year times the probability of false alarm. The cost of an explosion and the cost of false alarms are kept similar so the Monte Carlo analysis wouldn't overly emphasize one or the other.

There are a number of methods of selecting EDS sub-systems as candidate sub-systems for the design of a system. It should be noted that sometimes different methods lead to the same conclusions.

One method of analysis could be, but is not limited to, selecting an acceptable SPD and SPFA and then eliminating the EDS sub-systems with the lowest score.

Another method of analysis could be, but is not limited to, selecting an acceptable SPD and SPFA and then sort by CFOM and eliminate the most expensive combinations.

Alternately, the analysis could be done, but is not limited to, by selecting an acceptable SPD and SPFA and then sort by CFOM as before, and the sub-systems that appear most frequently in the most expensive combinations could be eliminated. For example, for SPD$\geq$90% and SPFA$\leq$1%, sub-systems that appear most frequently in the most expensive combinations could be eliminated from being candidate sub-systems.

Applying the analysis methods described above, sub-systems can be selected for a desired outcome.

It should be noted that, although EDS scores were presented for a group technologies, other technologies can be utilized. The system of this invention can utilize, but is not limited to, one of the following technologies: X-ray technologies, Neutron-Based Bulk Explosives Detection Technologies, Nuclear non-neutron based Bulk Explosive Technologies, Nuclear Quadrupole Resonance Technologies, and Trace Detection Technologies. The Nuclear non-neutron based Bulk Explosive Technologies include Gamma Resonance Technology (GRT) and Gamma Radiography. Other technologies (such as future technologies) can be utilized if available.

Figure 8:
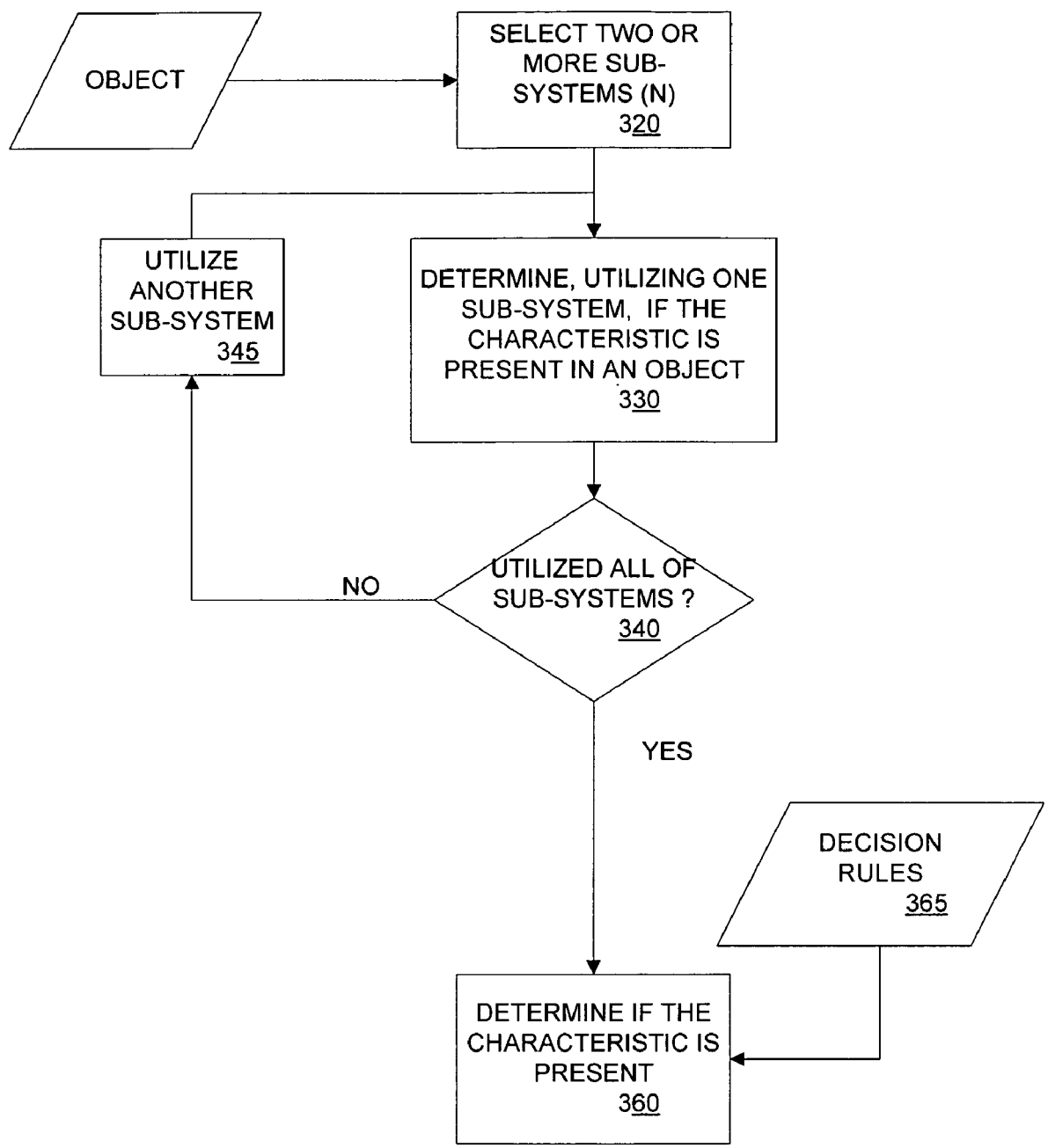
FIG. 8 depicts a flowchart of yet another embodiment of the method of this invention; and, FIG. 9 shows a schematic block diagram of another embodiment of the system of this invention.

Another embodiment of the method of this invention is shown in FIG. 8. Referring to FIG. 8, the embodiment of the method of this invention for detecting the presence of a characteristic in an object shown therein includes:
(a) providing two or more detection sub-systems (step 320),
(b) establishing a set of decision rules, to arbitrate between results of detection technologies and to detect the presence of the characteristic in the object (step 365),
(c) first determining, utilizing one of the two or more detection sub-systems (detection technologies), whether the characteristic is present in the object whether the characteristic is present in the object (step 330),
(e) repeating step (c) until all provided technologies have been utilized (step 340), and
(f) finally determining, utilizing said set of decision rules, whether the characteristic is present in the object (step 360).

In one embodiment, in which expert systems are used, the set of decision rules are obtained by selecting a candidate system including two or more detection subsystems, performing a number of measurements to determine a predetermined figure of merit indicating how well the system performs in determining whether the characteristic being tested for is present, repeating this procedure and generating the rules of the test results. In another embodiment, the rules are obtained by selecting a candidate system including two or more detection subsystems, performing a Monte Carlo analysis for detecting the presence of the characteristic being tested for, calculating a predetermined figure of merit, repeating this procedure to generate the knowledge database (obtaining the rules from the Monte Carlo results). Once the rules have been obtained to a desired degree of confidence, in one embodiment, the rules can be programmed as computer readable code. For example, the rules can be programmed as "if" "then" statements. (The algorithms and rules can be cast a form akin to an inference engine and into a rule based system for decisions or an "Expert System;" see, for example, P. Harmon, D. King, *Expert Systems—Artificial Intelligence in Business,* ISBN 0-471-80824-5, 1985).

In another embodiment in which a neural network is utilized to embody the set of rules, the data generated by embodiment such as the above-described is utilized to train the neural network. For example, in the embodiment described herein above, the candidate system/figure of merit pairs can be used to train the network. (See, for example, S. K. Rogers, M. Kabrisky, An Introduction to Biological and Artificial Neural Networks for Pattern Recognition, ISBN 0-8194-0534-5, 1991).

In both the expert system and the neural network approach, factors such as, but not limited to, the "region of greatest applicability" of any of the technologies can be taken into account.

In one instance, the characteristic is an undesired substance, for example an explosive, within the object. In that instance, the system of this invention can utilize, but is not limited to, one of the following technologies: X-ray technologies, Neutron-Based Bulk Explosives Detection Technologies, Nuclear non-neutron based Bulk Explosive Technologies, Nuclear Quadrupole Resonance Technologies, and Trace Detection Technologies. The Nuclear non-neutron based Bulk Explosive Technologies include Gamma Resonance Technology (GRT) and Gamma Radiography. Other technologies (such as future technologies) can be utilized if available.

Another embodiment of the system of this invention is shown in FIG. 9. Referring to FIG. 9, the embodiment of the system of this invention, for detecting the presence of one or more characteristics in an object, shown therein includes two or more detection subsystems 405, means for establishing a set of decision rules and decision means for determining whether the one or more characteristics are present in the object. In the embodiment in which the decision means include an expert system, an input device 420 (such as, but not limited to, a keyboard, a tape or optical disk or magnetic disk reader, an interface to a computer, or a carrier wave interface to a network) allows the inputting of data used to establish the set of decision rules, which is stored in the database 460 (in one instance, a memory 460 for storing data, where the memory includes a data structure including information resident in a database). A computer usable medium 430 has computer usable code embodied therein for implementing the set of rules and determining whether the one or more characteristics are present. The computer readable code causes one or more processors 410 to implement the set of rules and determine whether the one or more characteristics are present.

In the embodiment in which the decision means include a neural network, an input device 420 (such as, but not limited to, a keyboard, a tape or optical disk or magnetic disk reader, an interface to a computer, or a carrier wave interface to a network) allows the inputting of data used to train the network, which, in one embodiment, is stored in the database 460 (in one instance, a memory 460 for storing data, where the memory includes a data structure including information resident in a database). (Embodiments in which the data used to train the network is stored in the computer usable medium 430 are also within the scope of this invention.) The computer usable medium 430 has computer usable code embodied therein for implementing the neural network, such as, but not limited to, the number of nodes, the weight at each node, and the interconnections. The computer readable code causes the one or more processors 410 to implement the network and utilize the network to determine whether the one or more characteristics are present.

In another embodiment, the decision means are implemented using a minimization algorithm, such as, but not limited to, a genetic algorithm. In those embodiments, the computer usable medium 430 has computer readable code embodied therein that causes the one or more processors 410 to evaluate a cost function and apply the algorithm to minimize the cost function in order to select the combination of detection more processors 410 to determine whether the one or more characteristics are present.

In the embodiment shown in FIG. 9, the input device 420, the one or more processors 410, the database 460 and the computer usable medium 430 are operatively connected by means of a connection component 415 (the connection component may be, for example, a computer bus, or a carrier wave).

It should also be noted that although in the embodiments presented above the detection of the presence of a characteristic in an object is the detection of explosives inside objects, other embodiments of characteristics present in objects are also possible and within the scope of this invention. For example, embodiments in which characteristic is the absence of a property are within the scope of this invention.

Although the invention has been described with respect to various embodiments, it should be realized that this invention is also capable of a wide variety of further and other embodiments all within the spirit and scope of the appended claims.

What is claimed is:

1. A method for detecting a presence of a characteristic in an object, the method comprising the steps of:
    a) providing at least two detection technologies, each one of said at least two detection technologies providing a determination of the presence of the characteristic in the object;
    b) establishing a plurality of decision rules, to arbitrate between results of detection technologies and to detect the presence of the characteristic in the object;
    c) first determining, utilizing one of the at least two detection technologies, whether the characteristic is present in the object;
    d) repeating step c) until all provided technologies have been utilized;
    e) finally determining, utilizing said plurality of decision rules, whether the characteristic is present in the object.

2. The method of claim 1 wherein said plurality of rules comprises a neural network; and wherein the step of establishing said plurality of decision rules comprises the step of training the neural network.

3. The method of claim 1 wherein the characteristic is an undesired substance within the object.

4. The method of claim 3 wherein the undesired substance comprises an explosive.

5. The method of claim 4 wherein each one of said at least three detection technologies utilizes a technology selected from the group consisting of X-ray technologies, Neutron-Based Bulk Explosives Detection Technologies, Nuclear non-neutron based Bulk Explosive Technologies, Nuclear Quadrupole Resonance Technologies, and Trace Detection Technologies.

6. A system for detecting presence of at least one characteristic in an object, the system comprising:

at least two detection sub-systems, each one of said at least two detection sub-systems providing a determination of presence of said at least one characteristic in the object;

means for establishing a plurality of decision rules, said plurality of decision rules being utilized to arbitrate between results of detection technologies and for detecting the presence of the characteristic in the object; and decision means for determining, utilizing said plurality of decision rules, whether said at least one characteristic is present in the object.

7. The system of claim 6 wherein said decision means comprise a neural network; and wherein said means for establishing said plurality of decision rules comprise means for training said neural network.

8. The system of claim 6 further comprising:

at least one processor; and a memory for storing data for access by an application program being executed on said at least one processor, said memory comprising:

a data structure stored in said memory, said data structure including information resident in a database used by said application program and including said plurality of decision rules.

9. The system of claim 8 wherein said detection means comprise a computer usable medium having computer readable code embodied therein, said computer readable code being capable of causing said at least one processor to:

a) determine, utilizing one of said at least two detection technologies, whether said at least one characteristic is present in the object;

b) repeat step a) until all provided technologies have been utilized;

e) finally determine, utilizing said decision means, whether said at least one characteristic is present in the object.

10. The system of claim 9 wherein said decision means comprise a neural network; and wherein the means for establishing said plurality of decision rules comprises means for training the neural network.

11. The system of claim 9 wherein said decision means comprise an expert system.

12. The system of claim 6 wherein each one of said at least two detection sub-systems utilizes a technology selected from the group consisting of X-ray technologies, Neutron-Based Bulk Explosives Detection Technologies, Nuclear non-neutron based Bulk Explosive Technologies, Nuclear Quadrupole Resonance Technologies, and Trace Detection Technologies.

13. A method for providing data used to establish a plurality of decision rules to arbitrate between results of detection technologies and to detect presence of the characteristic in an object, the method comprising the steps of:

(a) providing a candidate system comprising at least two detection sub-systems, each one of said at least two detection sub-systems providing a determination of presence of said at least one characteristic in the object;

(b) performing a Monte Carlo analysis of detecting a presence of the at least one characteristic in an object;

(c) calculating a pre-defined figure of merit for the candidate system;

(d) providing the candidate system and the pre-defined figure of merit to a knowledge database.

14. The method of claim 13 wherein the step of providing the candidate system and the predefined figure of merit to the knowledge database comprises the step of providing the candidate systems and the predefined figure of merit as training data to a neutral network.

* * * * *